(12) United States Patent
Landis

(10) Patent No.: US 6,792,813 B1
(45) Date of Patent: Sep. 21, 2004

(54) RESISTANCE SPOT WELD CHECKING TOOL

(75) Inventor: Tod Michael Landis, Allendale, MI (US)

(73) Assignee: Practical Innovations LLC, Allendale, MI (US)

(*) Notice: Subject to any disclaimer, the term of this patent is extended or adjusted under 35 U.S.C. 154(b) by 0 days.

(21) Appl. No.: 10/335,713

(22) Filed: Jan. 2, 2003

(51) Int. Cl.[7] .............................................. G01N 3/20
(52) U.S. Cl. ...................................................... 73/850
(58) Field of Search ........................... 73/850, 855, 856

(56) References Cited

U.S. PATENT DOCUMENTS

| | | | | | |
|---|---|---|---|---|---|
| 4,167,264 A | * | 9/1979 | Kretzmeir | ..................... | 269/16 |
| 4,574,621 A | * | 3/1986 | Jegers | ....................... | 73/54.01 |
| 5,360,194 A | * | 11/1994 | Jacobson | .................... | 248/431 |
| 5,398,810 A | * | 3/1995 | Yao Wang | .................. | 206/373 |
| 6,032,621 A | * | 3/2000 | Tateshima | ............ | 123/41.82 R |
| 6,092,289 A | * | 7/2000 | Schad | ......................... | 30/112 |
| 6,666,832 B1 | * | 12/2003 | Carranza et al. | ............ | 600/587 |

OTHER PUBLICATIONS

Forest Wilson, Welding Inspection, Practicing in the Geo-Sciences, Jan. 15, 2000.

* cited by examiner

*Primary Examiner*—Max Noori

(57) ABSTRACT

Resistance welding is a process used to join metallic parts with electric current. A weld nugget is formed as the pieces are melted together. This weld nugget is normally circular in shape. Most welds are expected to be of a specific size based on a specific material thickness. The thinner the material, the smaller the weld nugget required. This reference tool allows the inspector to validate that the welds exceed the minimum requirement without the need to take measurements or the need to check specification sheets or use math skills. This tool also provides a visual and physical check of the weld nugget to verify compliance with the specification for the weld based on the material thickness.

6 Claims, 1 Drawing Sheet

RESISTANCE SPOT WELD CHECKING TOOL

BACKGROUND OF THE INVENTION

1. Field of the Invention

Resistance spot welds are required to be of sufficient size to meet the design expectations for the parts. Based primarily on automotive requirements, resistance spot welds are required to be larger on thicker materials and smaller on thinner materials. The tool described provides a simple way of checking the diameter of spot welds based on the thickness of the material being welded.

2. Related Art

In arc welding processes the use of Fillet Weld Gages allows inspectors to easily determine if welds conform to specification by providing a tool to gage the profile of the weld. The device shown in TTL News Jan. 15, 2000 measures the arc of a weld that has been made when affixing sheets or bars in a continuous welding profile. This device is used to gauge continuous welds and not spot welds.

A tool to do the same with Resistance Spot Welds was identified, and this patent application is the result.

SUMMARY OF THE INVENTION

Resistance Spots Welds are normally measured with calipers in two directions around the weld nugget. As in arc welding processes the use of Fillet Weld Gages allows inspectors to easily determine if welds conform to specification by providing a tool to gage the profile of the weld. A tool to quickly provide weld size validation was needed to get acceptable results quickly and easily. The device disclosed allows simple checking of the weld nugget or spot weld without mathematical calculations. Previously, a Technician would use calipers to measure the diameter of a spot weld or weld nugget, record the number, and then take a second measurement 90 degrees from the first measurement and record the second number. These two values would then be added together and an average diameter would be obtained. The technician would then measure the thickness of the material being welded together. Once the material thickness was obtained, the Technician would then consult a chart or standard for the material thickness to see if the diameter of the spot weld or weld nugget falls within a given diameter range. If the spot weld or weld nugget diameter falls within the range given in the standard or specification, then the spot weld was acceptable. While standards are generally known in the art, individual manufacturers or customers can have individual standards or custom standards.

The tool described herein gages the governing material thickness by fitting the thinnest material into the smallest slot. The Technician slides the welded material into the slots until the smallest slot that the material fits in is identified. No actual measurements are necessary and hence little chance for error. Once the smallest slot is identified, the Technician looks to the weld hole corresponding to the identified slot. The weld hole identified is the minimum diameter that is acceptable according to the specification.

The adjacent weld hole represents the required spot weld or weld nugget size. If the weld nugget cannot fit into the adjacent hole, then it exceeds the minimum weld size for that material thickness and is acceptable. If the weld nugget is smaller than the weld hole, and the tool can move back and forth indicating that the weld nugget diameter is smaller than the weld hole, the weld nugget is smaller than the minimum diameter for the specification and the weld nugget is not acceptable. The tool disclosed does not require any measurements or math skills. The inspection can be done visually by using this tool. Technicians do not need to make notes about measurements, calculate an average diameter nor do they need to have specification sheets or learn how to use them. The margin from Technician error is significantly reduced with the use of this tool.

A first object of the present inventions is to provide an easy way to check weld nugget diameters based on the thickness of the material being welded.

A second object of the present invention is to provide a simplified method of checking the specifications of weld nuggets without needing math skills.

Another object of the present invention is to provide a tool that does not require the use of tables or charts to verify any measurements obtained.

Another object of the present invention is to provide a tool that allows visual and physical reference of the weld nugget in relationship to a custom or standard specification.

These together with other objects of this invention, along with various features of novelty which characterize this invention, are pointed out with particularity in the claims annexed hereto and forming a part of this disclosure. For a better understanding of this invention, its operating advantages and the specific objects attained by its uses, reference should be had to the accompanying drawings and descriptive matter in which there is illustrated a preferred embodiment of this version of the invention.

Figure 1:
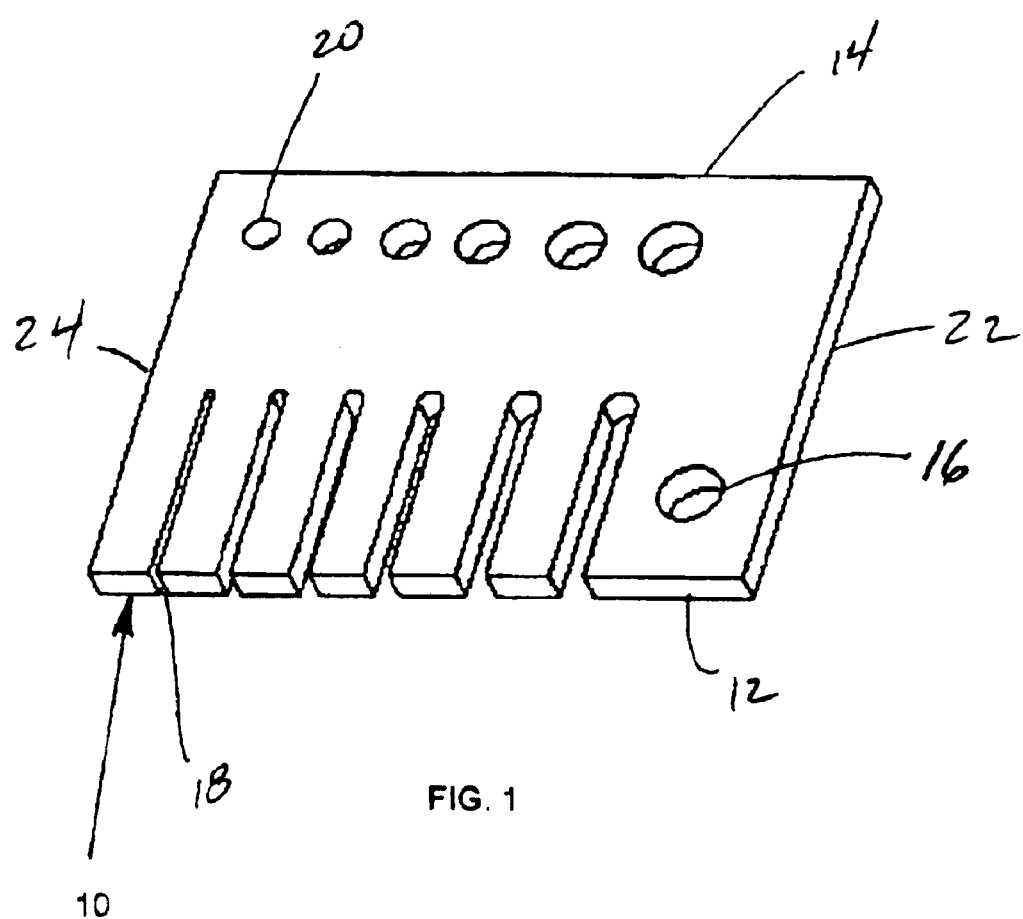
FIG. 1 shows a perspective view of one embodiment of the Resistance Spot Weld Checking Tool.

| | |
|---|---|
| 10 | Resistance Spot Weld Checking Tool |
| 12 | First Side |
| 14 | Second Side |
| 16 | Attachment Hole |
| 18 | Slot |
| 20 | Weld Hole |
| 22 | Third side |
| 24 | Fourth side |

DETAILED DESCRIPTION

FIG. 1 illustrates the resistance weld checking tool 10. The tool gages the governing material thickness by fitting the thinnest material into the smallest slot. The adjacent hole represents the required weld nugget size. If the weld nugget cannot fit into the adjacent hole, then it exceeds the minimum weld size for that material thickness and is acceptable. The first side 12 has multiple slots 18 that are used determine the governing metal thickness of the material that has been welded. The depth of these slots 18 is substantially the same. The second side 14 has multiple weld holes 20 that correspond to the slots 18 on the first side 12. The weld holes 20 are used determine sufficient weld nugget has been made by being smaller than the weld nugget being gaged. When the weld nugget being checked is larger than the weld holes 20, the weld nugget exceeds the minimum defined weld nugget size of the weld specification. The attachment hole 16 allows the resistance weld checking gage 10 to be attached to a key chain. The attachment hole 16 can be located near a third side 22 or a fourth side 24. The third side 22 and fourth side 24 are located between the first side 12 and second side 14.

What is claimed is:

1. A tool for measuring the diameter of resistance weld nuggets, the tool comprising:

a plate having a first side opposite a second side, a third side opposite a fourth side;

a plurality of varying width slots cut into the first side, the slots sized for measuring different material thicknesses of metal welded; and a plurality of circular holes corresponding in number to the plurality of slots, the circular holes located in a linear relationship from the corresponding slots and located near the second side, the circular holes diameter corresponding in size to the minimum weld nugget diameter for the corresponding material thickness as gauged by the corresponding slots.

2. The tool of claim 1, further comprising:

an attachment hole for attaching the tool to a key chain.

3. The tool of claim 1, further comprising:

the slots are cut perpendicular to the first side.

4. A tool for measuring the diameter of resistance weld nuggets, the tool comprising:

a plate having a first side opposite a second side, a third side opposite a fourth side;

a plurality of slots cut into the first side, the slots varying in size from the smallest width near the fourth side to a larger width near the third side, the slots sized for measuring different material thicknesses of metal welded; and a plurality of circular holes corresponding in number to the plurality of slots, the circular holes located in a linear relationship from the corresponding slots and located near the second side, the circular holes diameter corresponding in size to the minimum weld nugget diameter for the corresponding material thickness as gauged by the corresponding slots, the diameter of the circular holes varying from the smallest near the fourth side to the larger near the third side.

5. The tool of claim 4, further comprising:

an attachment hole for attaching the tool to a key chain.

6. The tool of claim 4, further comprising:

the slots are cut perpendicular to the first side.

* * * * *